United States Patent [19]

Behrens et al.

[11] 4,299,209
[45] Nov. 10, 1981

[54] VERTEBRAL IMMOBILIZATION AND EXTRICATION SUPPORT

[76] Inventors: James D. Behrens, 3355 S. Flower, No. 146, Lakewood, Colo. 80227; James W. Buckley, 4940 Estes Ct., Arvada, Colo. 80002

[21] Appl. No.: 34,178

[22] Filed: Apr. 27, 1979

[51] Int. Cl.$^3$ .............................................. A61F 5/04
[52] U.S. Cl. ........................ 128/87 B; 128/DIG. 15
[58] Field of Search .................. 128/90, 87 B, 89 R, 128/DIG. 15

[56] References Cited

U.S. PATENT DOCUMENTS

| | | | |
|---|---|---|---|
| 2,607,103 | 9/1952 | Davidson | 27/28 |
| 2,853,067 | 4/1958 | Puharich | 128/90 |
| 3,469,268 | 11/1969 | Phillips | 5/82 |
| 3,696,439 | 7/1972 | Durham | 128/90 |
| 3,707,734 | 3/1973 | Matthews | 5/82 |
| 3,732,863 | 4/1973 | Harrington | 128/84 C |
| 3,737,923 | 7/1973 | Prolo | 5/82 |
| 3,889,668 | 11/1975 | Ochs et al. | 128/134 |
| 4,024,861 | 8/1977 | Vincent | 128/87 R |
| 4,034,748 | 10/1977 | Winner | 128/87 R |
| 4,060,075 | 10/1977 | Blomer et al. | 128/90 |
| 4,143,654 | 4/1979 | Sherman | 128/87 R |

OTHER PUBLICATIONS

"Emergency Care", by H. Grant & R. Murray, 1971, R. J. Brady Co., p. 441.
Activeaid Handbill Advertisement, no date, applicant claims receipt of same in 1978.
Emergency Care & Transportation of the Sick & Injured, AAOS, 2nd Ed., 1977, Geo. Banta Co., Chap. 47, p. 377.

Primary Examiner—Robert W. Michell
Assistant Examiner—C. W. Shedd
Attorney, Agent, or Firm—Louis G. Puls, Jr.

[57] ABSTRACT

For maintaining cervical and spinal alignment during emergency immobilization, extrication, transportation, and radiological examination of a patient, a support used in combination with various fastening devices comprising a sheet with a curved cross-section made of radiotranslucent buoyant material which has a thin profile yet provides strong and rigid support. The sheet is contoured to support the patient's head, shoulders, and main body, preventing post-incident injury and discomfort. The margins of the support have a plurality of slots which serve both as handling means and as a means for attaching the fastening devices and are arcuately displaced for ease of access with minimal hazardous movement of the patient. Moreover, the head-supporting portion has a plurality of guide notches and a Velcro fastener for attaching fastening devices, with similarly arcuately displaced access. The support has a short form which is used for securing the upper torso under conditions which preclude the use of the long form. The long form of the support provides management of the full body during emergency extrication, transportation and radiological examination, for use in combination with the short form and for use as a litter.

7 Claims, 7 Drawing Figures

VERTEBRAL IMMOBILIZATION AND EXTRICATION SUPPORT

BACKGROUND OF THE INVENTION

The present invention relates to a vertebral immobilization and extrication device and, more particularly, to such a device especially fabricated for use with emergency spinal injury patients, such as those, for example, who are victims in motor vehicle accidents.

As emergency medical care has matured in recent years, awareness has grown that proper prehospital handling of trauma patients can be of vital importance in reducing the severity of ultimate neurological deficit due to spinal column injury. Such handling prior to admission to a medical facility includes assessment of the possible trauma involved, the immobilization and stabilization of the patient in a rigid position least likely to aggravate the injuries, extrication of the patient from the accident situation, and transport to the facility. The personnel and equipment involved in said handling must be such as to provide an optimal balance between caution and expedience, if beneficial results are to be achieved.

As discussed in U.S. Pat. No. 3,889,668 the prior art and current practice involves the use of flat rigid spine boards, with securing and handling means therein, in association with other devices such as cervical collars, body harnesses, and flexible straps. Such equipment should be designed to be simple and convenient enough to be rapidly applied to the patient, in order to minimize risk, and yet to be effective in immobilizing the patient from the time of extrication until completion of x-ray diagnostic examination at the medical facility.

Significant problems in current practice relating to said flat rigid spine board often result with respect to both rapid application and effective immobilization. A typical and frequently occuring instance requiring the use of the spine board is a motor vehicle accident in which a victim is seated in a closely confined position. In this case a short spine board is preferably placed behind the victim with a minimum of movement of the head, neck, and spine. Often, however, the victim is pressed closely to the back support of the seat which commonly has contoured lateral supports, such as in deep bucket seats. In such a situation, placement of the flat board, which is usually approximately three-fourths inch in thickness, becomes difficult or impossible without moving the victim substantially away from the back support of the seat, thereby increasing the risk of significant spinal column injury and consequent neurological deficit.

Moreover, once the flat board is in place, the straps used in immobilizing the patient are fastened to the board only with some difficulty and at further risk of spinal movement because the board and its strap-receiving holes are often closely pressed into the back support of the seat. A further problem may arise because access to hand-holding means is similarly limited, making cautious and rapid extrication more difficult. The prior art has recognized this problem and has attempted to alleviate it. For example, longitudinal runners or transverse cleats, such as disclosed in U.S. Pat. No. 4,034,748, are often attached to the reverse side of the flat spine board to allow better access to strap and hand holes; however, such additional structure contributes to the effective width of the board and may compound the difficulty of proper initial placement. During extrication, the flat board presents a large surface area when slid across relatively flat material, such as seat cushions, resulting in friction and possible snagging of the board edge.

A still further problem may occur when the patient is in a supine position while fastened to the flat board. In such an immobilized position, vomiting by the patient is a particular risk, since aspiration may result. Lateral rotation of the patient is the best means of preventing aspiration; however, in the case of a heavy patient and an insufficient number of attendants, a carefully controlled rotation is made difficult because of the necessary use of the full width of the flat board as a lever arm. A still further disadvantage of the flat board is the limited surface area of contact with the back of the patient. Excessive stress may be exerted on the vertebral articulation rather than evenly distributed along the rib cage and shoulders. Because only such limited contact area is acting, in concert with said harness and strap means, to stabilize the patient, some lateral shifting of the body may occur, for example during rotation, and twisting or other distortion of the spinal column may result in further injury and discomfort to the patient.

SUMMARY OF THE INVENTION

A general object of the present invention is to provide a new and improved vertebral immobilization and extrication device usable in emergency situations such as those described above.

A specific object of the present invention is to provide a new and improved vertebral immobilization and extrication device which allows both expeditious application and effective stabilization.

A further object of the present invention is to provide a new and improved vertebral immobilization and extrication device which may be utilized with various patient-fastening means.

An immobilization and extrication device constructed in accordance with the present invention comprises an elongated sheet which is arcuately formed in the lateral direction and which is approximately shaped and sized to conform with the human body. Said sheet is preferably made of radiotranslucent material which is laminately reinforced to be essentially rigid in the direction of its longitudinal axis of symmetry and resiliently flexible but firm in the direction of lateral curvature. Included in the lamination is sufficient buoyant material to render the sheet capable of flotation in water. The sheet is contoured into portions which approximately outline the patient's head, shoulders, and main body. The shoulder portion includes slots for shoulder fastening means, and the head portion includes notches along its lateral margins for receiving head fastening means. A standard Velcro fastener part is fixed on the convex side of the head portion. The main body portion is generally rectangular and includes preferably trapezoidally shaped slots along its margins which serve both for receiving body fastening means and for providing handling means gripped by the attendants. The length of the main body portion is either sufficient to support the torso of the patient, or alternatively, to support the torso, hips, legs, and feet of the patient.

A major advantage of the present invention over the prior art is that, because of its arcuate lateral contour and its relatively thin cross section, said spine board can be more readily slid into position in a confined area, more closely following the contour of the patient's back, and more effectively avoiding shifting the patient's spinal column and the consequent risk of further injury.

A further advantage of the present invention over the prior art is that, because of the close conformity of the emplaced spine board with the contour of the patient's back, access to the strap and hand slots along the lateral margins is more readily facilitated, the displacement of said slots being approximately three inches from the plane of the corresponding prior art flat board, hence said slots are less likely to be in closely-confining relation to surrounding materials.

A still further advantage of the present invention over the prior art is that during extrication, for example in pulling the patient-bearing spine board across closely-confining material, the curvature of said board presents less surface contact and less edge interference with said material, expediting said extrication with minimal unnecessary disturbance and discomfort to the patient.

A still further advantage of the present invention over the prior art is that in the event of vomiting by the patient while immobilized and supine on the spine board, the attendants can more easily reduce the risk of aspiration by rolling the patient and board laterally along the curvature of the board until the patient is facing downwardly with respect to gravity and said patient's air passages can be cleared. Such a maneuver can usually be accomplished by a single attendant, even in the case of a heavy patient.

A still further advantage of the present invention over the prior art is that said board is contoured to conform closely with the patient's back and thereby increasing the surface area of supporting and stabilizing contact. Such increased area enables the forces of support to be more widely distributed on the rib cage and shoulders of the patient, thereby reducing the forces along the vertebral articulation and hence reducing risk of further injury and patient discomfort.

Moreover the increased area of contact provides more effective stabilization against the shifting of the patient within said harness and strap means, thereby reducing the risk of spinal distortion and associated injury and patient discomfort.

Objects and advantages other than those set forth above will be apparent from the following description when read in connection with the accompanying drawings of a preferred embodiment, whose novel features are set forth with particularity in the appended claims.

DETAILED DESCRIPTION OF THE PREFERRED EMBODIMENTS

Figure 1:
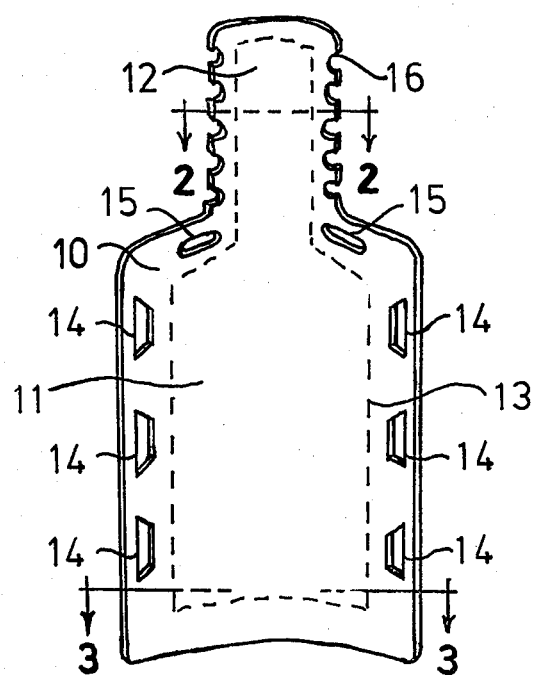
FIG. 1 is a perspective view illustrating the concave side of the preferred embodiment of the spine board according to the present invention.
Figure 2:
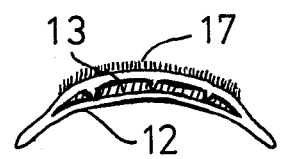
FIG. 2 is a cross-sectional view taken along the line 2—2 in FIG. 1.
Figure 3:
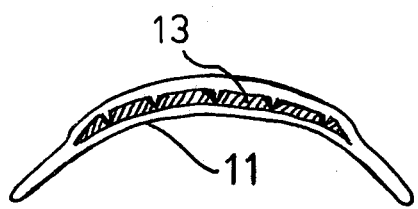
FIG. 3 is a cross-sectional view taken along the line 3—3 in FIG. 1.

In the drawings, corresponding parts are referred to with the same reference numerals even when the Figures show different embodiments of the same invention.

As herein embodied, a vertebral immobilization and extrication support board comprises an elongated sheet member 10 wherein a main body portion 11 and a head and shoulder portion 12 are formed of laminate material of woven glass fiber, plastic, or other radiotranslucent sheet material of comparable strength and rigidity, shaped and sized to roughly approximate the contours of the human body. The margins of said sheet member 10 essentially outline the human head, shoulders, and torso or lower body, whereas the lateral contour of said sheet member 10 is arcuately formed in a nearly circularly cylindrical sector to conform approximately to the human backside contour. Said lateral margins at the widest dimension are displaced by curvature about three inches from a reference plane tangent to the longitudinal symmetry axis of said sheet member 10. Said shoulder and head portion 12 is narrower than but has the same lateral radius of curvature as the main body portion 11.

Said laminate material envelops a core layer 13, in both portions 11 and 12, comprising a highly buoyant material. Such buoyant material is preferably composed of a single cross-grain ply of one-fourth inch balsa wood, segmented into fiber-mat reinforced rectangular sections in order to accommodate the lateral curvature. However, other buoyant materials as known in the art would be suitable. Said core layer 13 is also symmetric about said longitudinal axis with its side edges generally parallel to the adjacent edges of the enveloping laminations, and its area is approximately two-thirds of that of said enveloping laminations. The segments comprising the margin of said core layer 13 are beveled on the convex side to provide a smoother transition profile at the external surface, hence reducing friction and avoiding interference with surrounding materials during emplacement or extrication. The concave external surface is formed to be smooth throughout its curvature and preferably comprises an easily cleaned lamination material such as, but not limited to, glass fiber in a fine weave cloth. Said core layer provides sufficient buoyancy to the spine board to allow its flotation, such as would be useful, for example, with an accident victim in a vehicle in a body of water. Moreover, said core layer provides a flexibly firm, non-embrittling strengthening reinforcement to the relatively thin and lightweight sheet material. The preferred thickness of the spine board is approximately one-eighth inch at its margin and approximately three-eighths inch throughout its central part which includes the core layer.

Distributed along the opposing lateral margin areas of said main body portion 11 of the spine board are a plurality of slots 14. Said slots may be of conventional oblong shape, but are preferably each formed in the shape of an isosceles trapezoid wherein the longer of the parallel sides lies adjacent to the lateral edge of said portion 11. In any case, the dimensions of each slot are sufficiently long and wide to receive a hand as well as a harness strap or other conventional fastening means. Hence each slot 14 is capable of being used as a grasping or carrying handle for emplacement, extrication, and patient-bearing as well as being used for receiving fastening means 19 for the immobilization and stabilization of a patient 18.

Distributed along the opposing lateral edges of said head part of narrow portion 12 are a plurality of guide notches 16. Said notches 16 may be formed as v-shaped serrations but preferably are each of semi-circular shape with sufficient diameter to receive and retain in position a head strap or other standard fastening means 19. Near each opposing margin of the shoulder part of said narrow portion 12 is an oblong slot 15 parallel to said margin. Each said slot is of sufficient dimensions to receive a shoulder strap, harness strap or other standard fastening means 19.

On the convex side of said head part of narrow portion 12 is fixed, as by adhesive bonding, a rectangular strip 17 of Velcro fastener of sufficient size to largely cover the area between said opposing notches 16. As is well known, as such, Velcro fasteners are formed with one part having a mass of tiny loops and the other part having a mass of tiny hook-shaped projections. When the two opposite mating parts are pressed together, the projections engage the loops in a manner which establishes a tight bond between the two parts as against sliding movement of one part relative to the other. However, a user need only peel off one part from the other in order to disengage the bond. Said strip 17 comprises one such part with loop or hook-projections and can thus be used, in association with the said guide notches, to fasten head straps or other fastening means 19 on which are fixed, as by sewing, the said opposite mating part.

Figure 4:
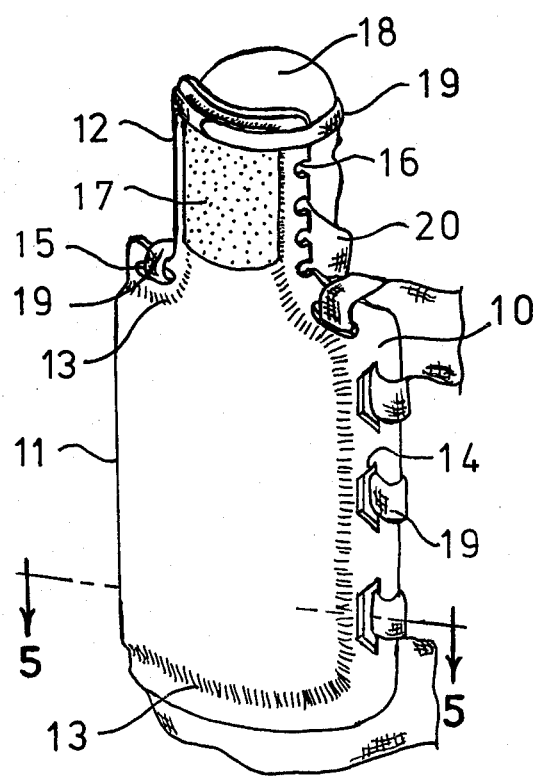
FIG. 4 is a perspective view of the convex side of the spine board as applied to a patient.
Figure 5:
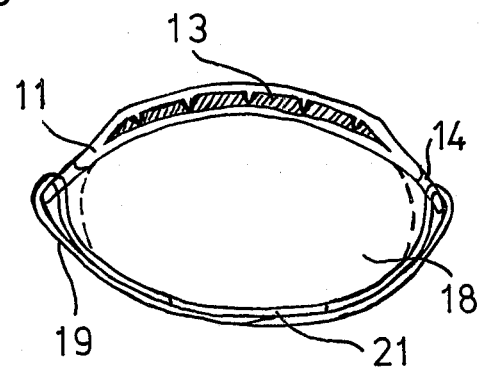
FIG. 5 is a cross-sectional view taken along the line 5—5 in FIG. 4.

Associated emergency medical devices which may be used to advantage with the present invention include various head bands, chin straps, and long strap means, such as those fastened by Velcro fasteners or aircraft-type buckles; various torso harnesses, such as disclosed in U.S. Pat. No. 3,889,668; various impromptu fastening means, such as adhesive bandaging or soft roller bandaging; various cervical collars, which provide further immobilization when neck injury is indicated, such as disclosed in U.S. Pat. No. 4,043,325; and neck support padding, such as a foam rubber neck roll. FIG. 4 indicates a cervical collar 20 in place on the patient 18. Said collar is well stabilized by the conforming curvature and resultant increased area of contact provided by the head and shoulder portion 12. FIG. 5 indicates the use of a torso harness 21 in which said harness straps function as said fastening means 19.

Figure 6:
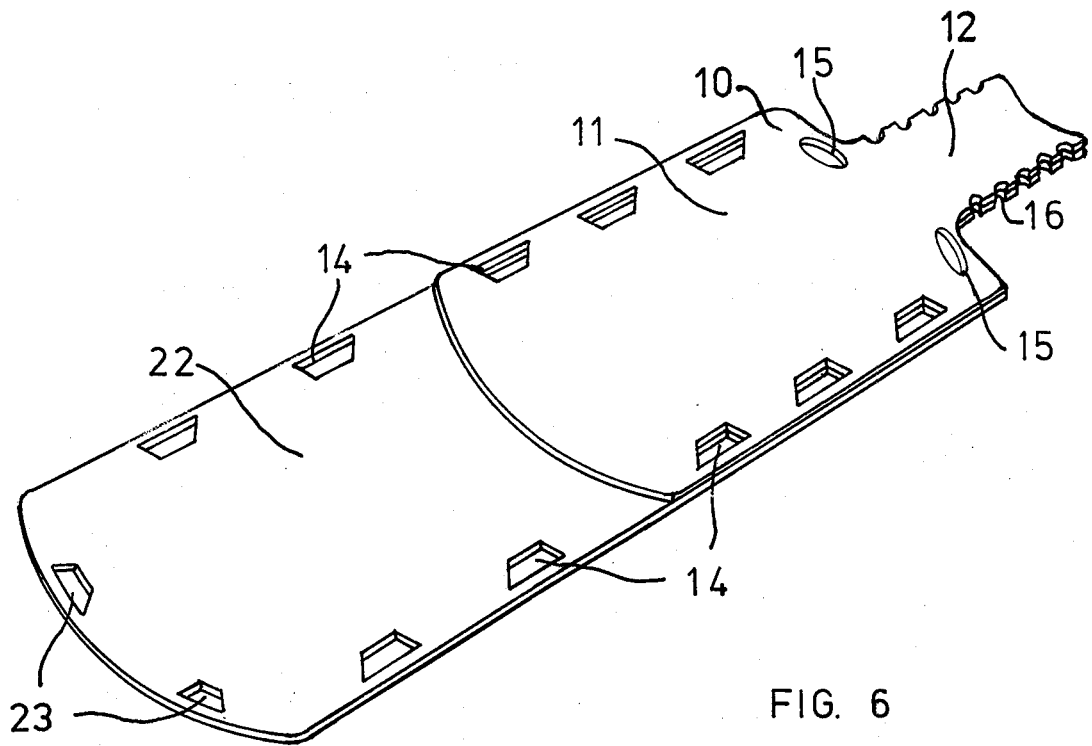
FIG. 6 is a perspective view of a nested combination of the two embodiments of the spine board according to the present invention.
Figure 7:
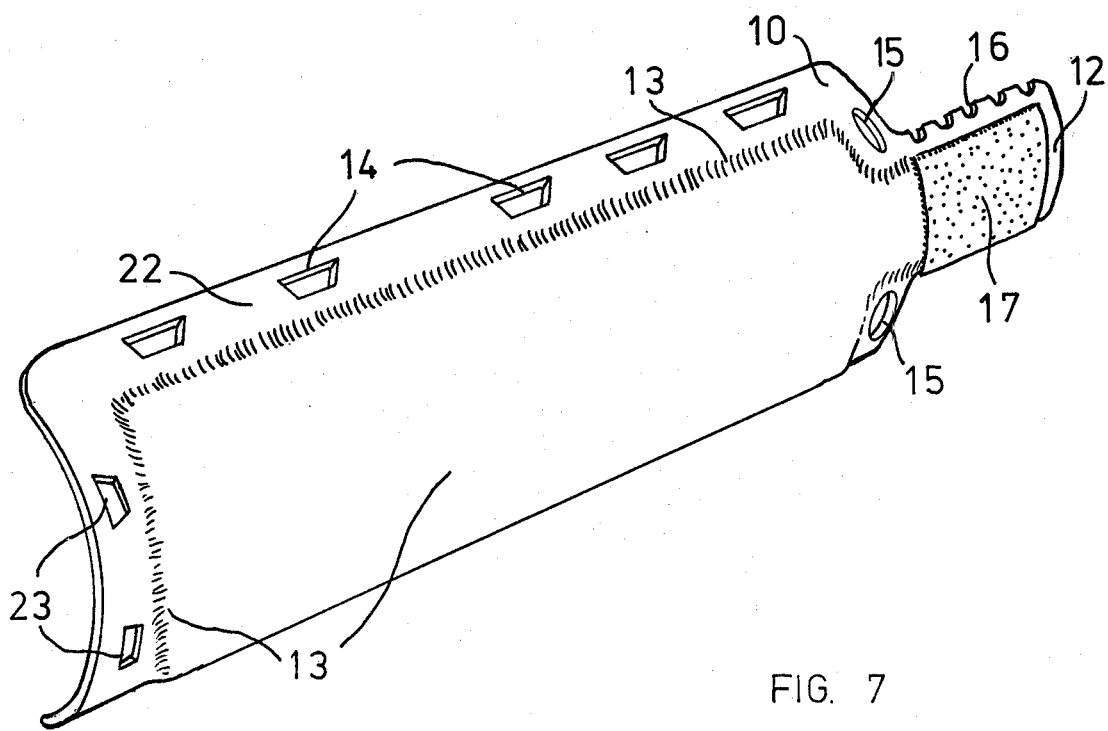
FIG. 7 is a perspective view of the convex side of an alternate embodiment of the spine board having an extended main body portion.

In FIG. 6 an alternate embodiment of the present invention wherein a long form of said spine board is shown in association with the short form of FIGS. 1-5. The upper portions 11 and 12 of said long form is identical with that of the short form. The extended portion 22 supports the hips, legs and feet of the patient, which are fastened in like manner as the torso by means of strap fastening means to slots 14. Additional hand-receiving slots 23 are provided at the foot edge of portion 22 in order to allow further handling and patient-bearing support.

It will be obvious to those skilled in the art that changes and modifications can be made in the embodiments of the invention as described without departing from the true spirit and scope of the invention as defined in the accompanying claims.

What is claimed is:

1. In an emergency vertebral immobilization, extrication, and transportation support, in combination with patient fastening means and related emergency medical devices, the improvement which comprises:

an elongated sheet member which is laterally arcuately formed of radiotranslucent material wherein said sheet is contoured into body conforming portions generally following the lateral curvature of the back and generally outlining the head, shoulders, and main body of the patient;

means for emplacing said sheet member tangentially along said lateral curvature into closely confining position with minimal movement of the patient wherein said sheet member has a thin and low friction cross section transverse to the tangential direction of emplacement and said arcuate sheet member generally conforms to the curvature of the interfacing surface between the patient's body and the closely confining material, such as that of an automobile seat;

means defining a plurality of slots distributed along opposing lateral margins of said main body portion of said sheet member with hand and fastener access means, requiring minimal movement of the patient, comprising an arcuate displacement of the sheet surface from the axial tangential plane and with said slots dimensioned to receive both fastening means and attendants' hands;

means defining a pair of slots each disposed along and parallel to the respective opposite margin of said shoulder contoured portion of said sheet member with hand and fastener access means, requiring minimal movement of the patient, comprising an arcuate displacement of the sheet surface from the axial tangential plane and with said pair of slots dimensioned to receive fastening means;

means defining a plurality of notches distributed along opposite edges of said head contoured portion of said sheet member with hand and fastener access means, requiring minimal movement of the patient, comprising an arcuate displacement of the sheet surface from the axial tangential plane and with said notches dimensioned to receive fastening means;

means defining hand and fastener access wherein a rectangular strip of Velcro fastener fixed on the convex side of said head-contoured portion of said sheet member is readily mated, with minimal movement of the patient, to head securing Velcro tipped straps guided through said notches, said access facilitated by means of the arcuate displacement of the sheet surface from the axial tangential plane;

means enabling the prevention of emesis aspiration of the patient when in a horizontal position wherein said sheet member is of sufficient curvature and strength to be rolled laterally to facilitate gravitational clearance of the patient's breathing passages;

means defining laminate enclosure of said radiotranslucent material about a buoyant and reinforcing beveled core layer flotation means.

2. A support as defined in claim 1 in which said radiotranslucent material comprises laminately bonded glass fiber woven fabric.

3. A support as defined in claim 2 in which said main body portion of said sheet member is of sufficient length to support the upper torso of the patient.

4. A support as defined in claim 2 in which said main body portion of said sheet member is of sufficient length to support the hips, legs, and feet of the patient and which is capable of being placed in nesting relationship with another support of the present invention.

5. A support as defined in claim 1 in which said radio-translucent material comprises plastic material.

6. A support as defined in claim 5 in which said main body portion of said sheet member is of sufficient length to support the upper torso of the patient.

7. A support as defined in claim 5 in which said main body portion of said sheet member is of sufficient length to support the higs, legs, and feet of the patient and which is capable of being placed in nesting relationship with another support of the present invention.

* * * * *